United States Patent [19]

Saito et al.

[11] Patent Number: 4,507,233

[45] Date of Patent: Mar. 26, 1985

[54] COLORED MOLECULAR WEIGHT MARKER

[75] Inventors: Hiraku Saito; Yasuo Suzuki; Katsumi Fujii; Kaoru Miyazaki; Takekazu Horio, all of Osaka, Japan

[73] Assignee: Oriental Yeast Co., Ltd., Tokyo, Japan

[21] Appl. No.: 485,375

[22] Filed: Apr. 18, 1983

Related U.S. Application Data

[63] Continuation of Ser. No. 256,398, Apr. 22, 1981, abandoned.

[51] Int. Cl.³ .................. B01D 57/02; C07G 7/04
[52] U.S. Cl. .................. 260/115; 252/408.1; 204/180 G; 204/180 R; 260/112 R; 260/121; 435/188; 435/213; 435/68; 435/69; 436/86; 436/88
[58] Field of Search .................. 260/112 R, 115, 121; 435/188, 213; 436/86, 88; 204/180 R, 180 G; 252/408.1

[56] References Cited

U.S. PATENT DOCUMENTS 4,107,014  8/1978  Suzuki et al. .................. 260/112 R
4,356,072  10/1982  Saito et al. .................. 204/180 G

OTHER PUBLICATIONS

Fish et al., J. Biol. Chem., 244, pp. 4989–4994, 1969.
Payne, Biochem. J., 135, pp. 867–873, 1973.
Chem. Abstracts, 81:164897w, Dupré et al., 1974.

*Primary Examiner*—Howard E. Schain
*Attorney, Agent, or Firm*—Browdy and Neimark

[57] ABSTRACT

Colored proteins having a known molecular weight of 1800 to 321200 are prepared by coupling monomers of a colored protein having a known molecular weight or by coupling a colored protein having a known molecular weight with a colorless protein having a known molecular weight. At least two proteins are selected from the so prepared colored proteins and used as a colored molecular weight marker. This colored molecular weight marker is used for determination of the molecular weight of a protein having an unknown molecular weight, and can also be used as a reference protein for purification of a protein having a known molecular weight.

12 Claims, 2 Drawing Figures

COLORED MOLECULAR WEIGHT MARKER

This application is a continuation of application Ser. No. 256,398, filed 4/22/81, abandoned.

BACKGROUND OF THE INVENTION (1) Field of the Invention

The present invention relates to a novel colored molecular weight marker having a broad applicable molecular weight range. More particularly, the present invention relates to a broad-range molecular weight marker enabling measurement of molecular weights in a very broad range of from very low molecules to macromolecules.

(2) Description of the Prior Art

In the fields of biochemistry and clinical assay, an SDS gel electrophoresis method and a molecular sieve chromatography method have recently attracted attention as means for separation, purification and analysis of proteins. According to the SDS gel electrophoresis method, a polyacrylamide containing SDS (sodium dodecyl sulfate or sodium lauryl sulfate) is used as a support and the molecular weight of a protein is measured according to the electrophoresis utilizing the molecular sieve action of the polyacrylamide. This method was first reported by Sapiro et al. and Weber, Osborn (J. Biol. Chem., 244, page 4406, 1969) and Neville et al. then proposed improvements of this method.

When a protein is treated with SDS, the protein is dissociated into subunits and the subunits are surrounded by SDS to form an SDS-protein composite. Accordingly, the protein comes to have a negative charge while the protein loses its inherent charge. Since SDS is coupled with the protein at a substantially constant rate, the negative charge density of the protein becomes constant.

When the electrophoresis is carried out by using a polyacrylamide gel having a molecular sieve action as a support, the protein migrates toward the anode and the mobility of the protein depends only on the size of the protein molecule. Therefore, measurement of the molecular weight of a protein is based on the principle in which the migration distance of a protein-SDS composite in an SDS-containing gel is measured, the measured distance is compared with the migration distance of a reference protein having a known molecular weight, the relative migration distance is calculated and the molecular weight is determined from the calculated relative migration distance.

According to this method, proteins can be separated and purified by utilizing the difference of the molecular weights and the molecular weight of a protein to be analyzed can be determined from the migration distance of a reference protein in the gel. Accordingly, this method is very valuable as a means for analyzing proteins.

Crosslinked dextran developed by Porath and Flodin (supplied under the tradename "Sephadex" by Pharmacia Co., Sweden) is now available very easily, and separation of proteins by using Sephadex is now one of the basic techniques in the field of biochemistry. According to this method, substances can be fractionated based on the difference of protein molecular weights, and this method is ordinarily called "molecular sieve chromatography". This method also is used for determination of the molecular weights, and the method of P. Andrews [Journal of Biochemistry, 91, page 222 (1964)] is utilized. As the support, not only Sephadex but also gel particles of polyacrylamide and agarose have been developed and are now commercially available.

Each of the particulate gels used for molecular sieve chromatography has a three-dimensional crosslinked structure which has a certain mesh size distribution. Accordingly, molecules having a size larger than the size of all the meshes are completely inhibited from intruding into particles while molecules having a size smaller than all the mesh sizes are allowed to freely diffuse into particles. The migration speed in the gel is determined according to the coefficient of distribution between the two phases, and the smaller is the size of the molecule, the lower is the migration speed in the gel. Furthermore, molecules are dissolved out in the order of the molecule size. Therefore, according to this method, various proteins can be separated and purified based on differences of molecular weights and simultaneously, the molecular weight of a protein having an unknown molecular weight can be determined by comparing the amount of this protein dissolved out with the amount dissolved out of a reference protein having a known molecular weight.

When proteins are separated and purified according to the above-mentioned SDS electrophoresis method and molecular sieve chromatography method, determination of molecular weights of various proteins is indispensable, and if a reference protein having a known molecular weight is used, the molecular weights of various intended proteins can be determined by comparing the migration distances of these proteins with that of the reference protein.

The reference protein used for this purpose is ordinarily called "molecular weight marker". Conventional molecular markers are prepared by combining various colorless proteins differing in their molecular weight, which have been separated from natural substances. If a colorless protein is used, the operation of measuring the molecular weight cannot be performed under naked eye observation. Furthermore, a complicated operation of coloration is necessary in the final stage, with the result that a long time is required for completion of the measurement of the molecular weight.

SUMMARY OF THE INVENTION

The present inventors have researched with a view to developing means for measuring molecular weights very simply and precisely in a short time in the above-mentioned SDS electrophoresis method and molecular sieve chromatography method, thereby facilitating analysis of proteins to be tested, and as the result, they have succeeded in obtaining broad-range colored molecular weight markers by coupling monomers of a colored protein having a known molecular weight or by coupling a colorless protein having a known molecular weight with a colored protein having a known molecular weight.

BRIEF DESCRIPTION OF THE DRAWINGS

In FIG. 1, symbols A, B, a, b, c, d, e, f and g represent component A in the rat serum, component B in the rat liver extract, a monomer of cytochrome Cl, a dimer thereof, a trimer thereof, a tetramer thereof, a heptamer thereof, a hexamer thereof and a nonamer thereof, respectively, and mark indicates that the dyeing degree of the protein is high and mark indicates that the dyeing degree of the protein is low.

In FIG. 2, symbols h, i, j, X and Y represent a decamer (having a molecular weight of 24,110) of a hempolypeptide formed by treating cytochrome C with chymotrypsin, a cytochrome C-albumin composite (having a molecular weight of $8.0 \times 10^4$), a dimer (having a molecular weight of $1.6 \times 10^5$) of a cytochrome C-albumin composite, hexokinase and glucose-6-phosphate dehydrogenase, respectively.

DETAILED DESCRIPTION OF THE PREFERRED EMBODIMENTS

Figure 1:
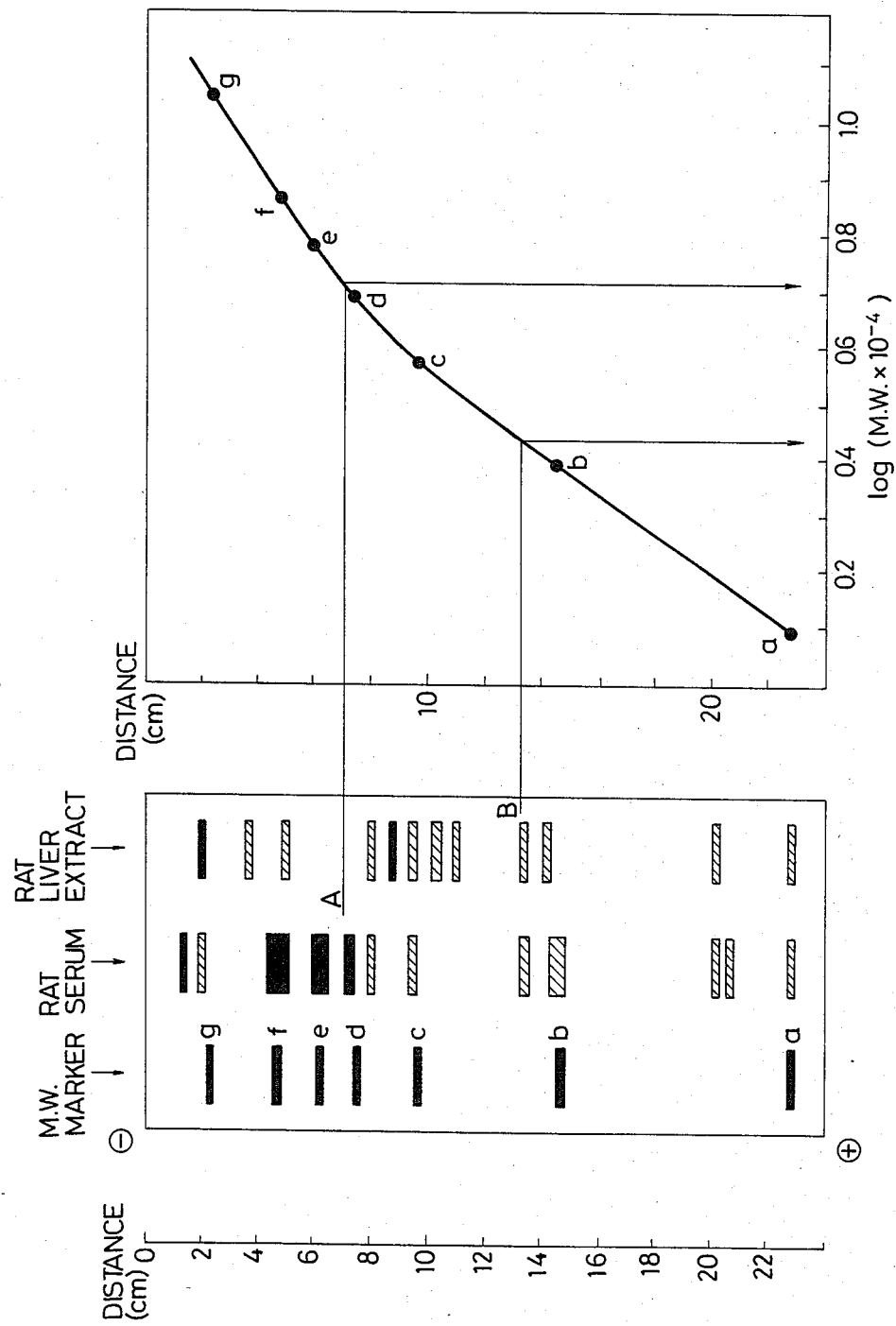
FIG. 1 is a diagram illustrating the results of Example 1 where the molecular weights of proteins present in rat serum and rat liver extract were determined according to the SDS gel slab electrophoresis method using the molecular weight marker of the present invention.

Colored proteins are used as the substrate of the molecular weight marker of the present invention, and, as such colored protein, there can be mentioned, for example, cytochromes C derived from organisms, myoglobin, hemoglobin, flavin protein and copper protein. Among these colored proteins, cytochromes C are especially preferred because they are hardly decomposed or modified by various treatments. Typical instances of the cytochrome C are shown in the following Table.

TABLE

| Kind of Protein | Source | Molecular Weight |
| --- | --- | --- |
| cytochrome C | equine heart muscle | 12,300 |
| cytochrome $C_2$ | Rhodopseudomonas palustris | 12,000 |
| cytochrome $C_2$ | Rhodospirillum rubrum | 12,800 |
| cytochrome $C_2$ | Rhodopseudomonas sphaeroides | 1,200 |

Among cytochromes C, equine heart muscle cytochrome C is most preferred, because the molecular weight is determined as 12,300, it is easily available at a low cost, it has a clear color, that is, a brown color in case of the oxidation type or a pink color in case of the reduction type, and because it is very stable.

However, since equine heart muscle cytochrome C contains 18 lysine units in one molecule as basic amino groups, it has an isoelectric point of 10.6 and is defective in that it is specifically adsorbed on various carriers such as Sephadex. This defect can be eliminated by acetylating or succinylating lysinoamino residues contained in the molecule of cytochrome C to change the isoelectric point to 5.0.

In the present invention, a colored protein having a low molecular weight can also be used. This low-molecular-weight colored protein is prepared by treating a colored protein such as mentioned above with a protein decomposition enzyme. As the protein decomposition enzyme, there can be mentioned trypsin and chymotrypsin.

This reaction is accomplished by adding a specific amount of a protein decomposition enzyme to a buffer solution of a colored protein having a certain concentration and maintaining a certain temperature (20° to 60° C.). The reaction is completed within 2 to 30 hours. The intended colored protein having a low molecular weight can be obtained by purifying the obtained liquid reaction mixture by using an ion exchanger and a molecular sieve gel filtering agent. For example, if equine heart muscle cytochrome C is treated with trypsin according to this method, a colored protein having a molecular weight of 1,800 is obtained, and if equine heart muscle cytochrome C is treated with chymotrypsin, a colored protein having a molecular weight of 2,400 is obtained.

As the colorless protein having a known molecular weight that is used in the present invention, there can be mentioned, for example, egg albumin, bovine serum albumin, lysozyme, chymotrypsinogen, aldehyde dehydrogenase and lactic acid dehydrogenase. Among them, bovine serum albumin is especially preferred because the molecular weight is determined as 68,000 and it is very stable.

A broad-range colored molecular weight marker of the present invention is prepared by using the foregoing proteins having a known molecular weight according to the following methods.

METHOD 1

A monomer of a colored protein having a known molecular weight is prepared and this monomer is polymerized to an oligomer such as a dimer or trimer.

METHOD 2

A colored protein having a known molecular weight is coupled with another colored protein having a known molecular weight or a colorless protein having a known molecular weight to form a monomer of the protein composite, and the monomer is converted to an oligomer such as a dimer, a trimer, a tetramer or a heptamer.

METHOD 3

A colored protein having a known molecular weight is converted to an oligomer such as a dimer or a trimer, the oligomer is coupled with a colorless protein having a known molecular weight, and if desired, the resulting composite is converted to an oligomer such as a dimer, a trimer or a tetramer.

Oligomerization of the colored protein or coupling of the colored protein with a colorless protein is accomplished by a treatment with a protein crosslinking agent. As the protein crosslinking agent, there can be mentioned, for example, diethyl pyrocarbonate and glutaraldehyde.

The reaction is accomplished by adding a specific amount of the protein crosslinking agent to a solution containing at a certain concentration the colored protein or its mixture with the colorless protein and vigorously stirring the mixture. The reaction is completed within 1 to 3 hours.

Coupling of the colored protein with the colorless protein and oligomerization of the resulting composite can similarly be accomplished according to the above-mentioned method. Even an ultra-high-molecular-weight polymer can be obtained, and the molecular weight is precise and handling, such as purification, is very easy. Accordingly, this method is very valuable.

In the reaction mixture liquid, there are contained various composites, for example, a composite comprising one molecule of the colored protein and one molecule of the colorless protein, a composite comprising two molecules of the colored protein and one molecule of the colorless protein and a composite comprising two molecules of the colored protein and two molecules of the colorless protein. If this reaction mixture liquid is purified by molecular sieve chromatography using a gel filtering agent, various molecular weight markers can be obtained.

Colored proteins different in the molecular weight in a very broad range can be obtained according to the above-mentioned method, and a molecular weight marker of the present invention is ordinarily formed by using at least colored proteins selected from these colored proteins. Of course, only one colored protein having a specific molecular weight is selected and used as a mark of a specific molecular weight.

Analysis of proteins by using the so obtained molecular weight marker is performed according to the following procedures. When the molecular weight of a sample protein is known, since the position of the intended protein in the gel is determined from a curve illustrating the relation between the molecular weight of the protein determined in advance by using the molecular weight marker of the present invention and the mobility of the protein, this portion is cut from the curve and used for necessary measurements.

When the molecular weight of a protein having an unknown molecular weight is measured, the protein is dyed and the measurement is carried out according to the same method as described above.

When gels having the same composition are subjected to the SDS gel electrophoresis under the same conditions, since the composition of the polyacrylamide support is not changed, it is considered that various proteins undergo the same molecular sieve action, and therefore, it is not always necessary to cause the molecular weight marker to flow simultaneously with the sample. In other words, there may be adopted a method in which the molecular weight marker is independently subjected to electrophoresis in a different gel. This method is advantageously adopted when many samples are simultaneously analyzed.

The molecular weight marker of the present invention can be utilized for measuring the molecular weights of various proteins in molecular sieve chromatography using dextran, polyacrylamide or agarose according to the following procedures. When the molecular weight marker and sample are subjected to molecular sieve chromatography, the molecular weight marker is subjected to the molecular sieve action of the support and respective components are gradually dissolved out from the column in the order of the molecular weight. If the absorbance is measured at a wave length of the chromophoric group of the protein (416 nm or 550 nm in case of cytochrome C), the amount dissolved out of the colored protein having the corresponding molecular weight can be measured without any complicated measurement operation, and there can be obtained a curve illustrating the relation between the molecular weight of the protein and the amount of the protein dissolved out into the gel.

Analysis of proteins by using the above-mentioned molecular weight marker is performed according to the following procedures. When the molecular weight of the sample protein is known, the amount dissolved out of the intended protein (the position in the fraction tube of the column) can directly be determined from the curve illustrating the relation between the molecular weight of the protein and the amount of the protein dissolved out in the gel, which is obtained in advance by using the molecular weight marker of the present invention. Accordingly, in this case, this portion is cut out from the curve and is used for necessary measurements. For example, when it is intended to separate a protein having a molecular weight of 76,500 from the sample and purify this protein, the sample is mixed with a colored molecular weight marker having a molecular weight higher than that of the intended molecular weight (for example, an albumin-cytochrome C composite having a molecular weight of 80,300) and a colored molecular weight marker having a molecular weight lower than that of the intended molecular weight (for example, an albumin-hempolypeptide dimer composite having a molecular weight of 72,822), and the mixture is packed in a molecular sieve chromatography column and the elution treatment is carried out. Thus, the intended protein is dissolved out between the two colored molecular weight markers and the intended protein can easily be isolated and purified.

When the molecular weight of the sample protein is unknown, necessary measurements are carried out with respect to all the fractions, and the position of the intended protein in the column is determined. Then, the molecular weight of the intended protein is determined from the curve illustrating the molecular weight of the colored protein and the mobility in the same manner as described above. Simultaneously, a band of the colored protein in the column can be observed with the naked eye and it is possible to discriminate whether or not the molecular sieve chromatography is carried out in good conditions.

As will be apparent from the foregoing description, when the broad-range colored molecular weight marker of the present invention is used for SDS electrophoresis and molecular sieve chromatography of proteins, the molecular weights can be determined very simply with a high measurement precision, and the separation state can be observed with the naked eye and the intended protein can easily be discriminated from the reference protein. Accordingly, the present invention makes great contributions to development and progress of SDS electrophoresis and molecular sieve chromatography.

The present invention will now be described in detail with reference to the following Preparation Examples and Examples.

PREPARATION EXAMPLE 1

A 0.1M phosphate buffer solution (having a pH value of 7.0) containing 50 mg/ml of equine heart muscle cytochrome C (having a molecular weight of 12,300) was prepared, and while glutaraldehyde was gradually added to the solution so that the final concentration was 0.1%, the mixture was violently stirred. Reaction was carried out at room temperature for 1 to 3 hours.

Then, NaBH$_4$ (sodium borohydride) was added to the reaction mixture so that the final concentration was 2 mM, and reduction was thus conducted to convert the Schiff base in cytochrome C to a secondary amine.

Cytochrome C contains in the molecule free NH$_2$ groups of lysine and arginine as basic amino acids, and these amino groups form Schiff bases by reaction with the CHO group of glutaraldehyde, whereby dimer through hexamer of cytochrome C were formed at certain concentrations.

The so obtained liquid reaction mixture was subjected to molecular sieve chromatography using a support of polyacrylamide and agarose to obtain purified monomer (having a molecular weight of 12,300), dimer (having a molecular weight of 24,600), trimer (having a molecular weight of 36,900), tetramer (having a molecular weight of 49,200), heptamer (having a molecular weight of 61,500) and hexamer (having a molecular weight of 73,800). When the molecular weights of these oligomers or polymers were determined according to SDS electrophoresis using natural colorless proteins, it was found that they had the above-mentioned molecular weight, respectively.

When the dimer of cytochrome C (having a molecular weight of 24,600) separated and purified by molecular sieve chromatography was polymerized, a tetramer (having a molecular weight of 49,200), a hexamer (having a molecular weight of 73,800) and an octamer (having a molecular weight of 98,400) could be separated and purified. When the trimer of cytochrome C (having a molecular weight of 36,900) was polymerized, a hexamer (having a molecular weight of 73,800) and a monamer (having a molecular weight of 110,700) could be separated and purified.

The method illustrated in this Example is a method suitable for production of colored proteins as molecular weight markers for SDS electrophoresis.

PREPARATION EXAMPLE 2

When a polymer of cytochrome C such as mentioned above is used as a molecular weight marker in molecular sieve chromatography, since equine heart muscle cytochrome C has an isoelectric point of 10.6 and contains large quantities of basic amino acids, especially lysine, it is specifically adsorbed on dextran and agarose that are used in molecular sieve chromatography. Accordingly, the $\epsilon$-amino groups of lysine units in the molecule of cytochrome C should be chemically modified. As means for chemical modification of lysine, there can be mentioned acetylation and succinylation methods.

The cytochrome C polymer obtained in Preparation Example 1 was dissolved in water to obtain an aqueous solution having a concentration of 24 g/ml, and acetic anhydride or succinic anhydride was added to the solution so that the final concentration was 50 mM. Then, 1N NaOH was added to the solution so as to maintain a neutral condition, and the reaction was then carried out. By this treatment, the $\epsilon$-amino group of lysine in equine heart muscle cytochrome C was acetylated or succinylated and the modified polymer of equine heart muscle cytochrome did not show a specific adsorbability to the above-mentioned supports any more. If this polymer was subjected to molecular sieve chromatography together with a protein having a known molecular weight to determine the molecular weight, it was found that the determined molecular weight was substantially equal to the calculated value.

The method illustrated in this Example is a method suitable for production of colored proteins as molecular weight markers for molecular sieve chromatography.

PREPARATION EXAMPLE 3

Equine heart muscle cytochrome C (having a molecular weight of 12,300) and bovine serum albumin (having a molecular weight of 68,000) were dissolved in a 0.1M phosphate buffer solution (having a pH value of 7.0) at concentrations of 50 mg/ml and 125 mg/ml, respectively, and glutaraldehyde was gradually added to the solution so that the final concentration was 0.125%. Reaction was carried out at room temperature with violent stirring for 1 to 3 hours.

$NaBH_4$ was added so that the final concentration was 2 mM and reduction was effected in the same manner as described in Preparation Example 1, whereby a stable cytochrome C-albumin composite (having a molecular weight of 80,300) was obtained.

Cytochrome C and albumin contain in the molecule basic amino acids such as lysine and arginine, and free $NH_2$ groups of these amino acids form Schiff bases with the CHO group of glutaraldehyde to form a cytochrome C-albumin composite.

The isoelectric points of equine heart muscle cytochrome C and bovine serum albumin are 10.6 and 4.9, respectively. It was found, however, that the isoelectric point of the so obtained cytochrome C-albumin composite was 6.2. The obtained liquid reaction mixture was separated by using an ion exchanger to recover the cytochrome C-albumin composite.

When the molecular weight of this composite was determined according to molecular sieve chromatography and SDS electrophoresis using a natural colorless protein having a known molecular weight, it was found that the molecular weight was equal to the above-mentioned value (80,300).

When this cytochrome-albumin composite (having a molecular weight of 80,300) was further polymerized, molecular weight markers having an increased molecular weight, such as a dimer (having a molecular weight of 160,600), a trimer (having a molecular weight of 240,900) and a tetramer (having a molecular weight of 321,200), could be separated and purified.

Molecular weight markers having a much higher molecular weight, which could hardly be separated and purified from a polymer of cytochrome C, could be obtained from the so obtained cytochrome C-albumin composite.

These molecular weight markers could be effectively used in molecular weight sieve chromatography.

PREPARATION EXAMPLE 4

Equine heart muscle cytochrome C (having a molecular weight of 12,300) was dissolved in a 0.2M phosphate buffer solution (having a pH value of 7.0) so that the final concentration was 1%, and crystalline powder of chymotrypsin was added to the solution so that the final concentration was 0.005%. Reaction was carried out at 25° C. for 24 hours, and after completion of the reaction, DFP (diisopropyl fluorophosphate) was added as a protease inhibitor so that the final concentration was 1 mM. Thus, the enzymatic reaction was completed.

Chymotrypsin as a protease has a function of hydrolyzing a peptide linkage of an amino acid adjacent to the carboxyl group (COOH) of tyrosine, phenylalanine, tryptophan, histidine or the like. Accordingly, if equine heart muscle cytochrome C is treated with chymotrypsin, hempolypeptide can be obtained.

The molecular weight of the so obtained hempolypeptide was 2,411. If this polypeptide was polymerized according to the same method as described in Preparation Example 1, a dimer of hempolypeptide having a molecular weight of 4,822 was obtained.

Hempolypeptides obtained according to the above-mentioned method contain large quantities of basic amino acids such as lysine and it is specifically adsorbed on a support for molecular sieve chromatography. Accordingly, the $\epsilon$-amino group of lysine should be acetylated or succinylated according to the same method as described in Preparation Example 2.

The hempolypeptide prepared according to the above-mentioned method and oligomers thereof could be utilized as molecular weight markers consisting of a low-molecular-weight colored protein for molecular sieve chromatography.

Examples of the present invention will now be described.

EXAMPLE 1

Serum separated from rat serum and rat liver extract were subjected to SDS gel slab (gel plate) electrophoresis (the apparatus used was one supplied by Koike Seisakusho) according to the following method by using as the molecular weight marker a combination of monomer, dimer, trimer, tetramer, heptamer, hexamer and nonamer of equine heart muscle cytochrome C (having molecular weights of 12,300, 24,600, 36,900, 49,200, 61,500, 73,800 and 110,700, respectively).

To pure water were added 37.5 g of acrylamide, 1 g of N,N'-methylene-bis-acrylamide, 13.6 g of tri-aminomethane, 0.3 g of SDS (sodium dodecylsulfate) and 150 mg of ammonium persulfate to obtain 300 ml of a solution. The pH value was adjusted to 8.8 by hydrochloric acid. The solution was sufficiently mixed and degasified by a suction desiccator, and 0.15 ml of N,N,N',N'-tetramethylethylene diamine was added to the solution and sufficiently mixed. Then, the resulting mixture was filled in a completely sealed flat plate tank (30 cm in the length, 17 cm in the width and 8 mm in the thickness) in a depth of about 26 cm, and polymerization was carried out to obtain a separation gel.

After formation of the separation gel by polymerization, a concentration gel was prepared according to the following procedures. In pure water were dissolved 0.5 g of acrylamide, 0.12 g of N,N'-methylene-bis-acrylamide, 20 mg of SDS, 0.3 g of tris-aminomethane and 40 mg of ammonium persulfate to form 20 ml of a solution. The pH value was adjusted to 6.8 by hydrochloric acid. The solution was sufficiently mixed in a flask and degasified by a suction desiccator, and 0.02 ml of N,N,N',N'-tetraethylene diamine was added to the solution and sufficiently mixed. The mixture was quietly superposed in a height of about 2 cm on the separation gel formed in advance by polymerization. A spacer for filling a sample was inserted into the plate and polymerization was carried out. The so formed separation gel and concentration gel were used as the gel for SDS gel slab electrophoresis.

Blood was sampled from the rat artery and coagulated at 36° C. for 1 hour and centrifugal separation was carried out under 3,000×g for 10 minutes to obtain 2.1 μl of a supernatant (70 mg of proteins per ml of the supernatant), which was used as a sample solution. Separately, a 20 mM phosphate buffer solution was added to the rat liver, and the mixture was homogenized. The resulting homogenate was subjected to centrifugal separation under 100,000×g for 1 hour to obtain 7.5 μl of a supernatant (20 mg of proteins per ml of the supernatant), which was used as a sample solution.

Then, 30 μg each of the above-mentioned seven components of the molecular weight marker, 150 μg of the rat serum and 150 μg of the rat liver extract were separately injected into the top end concentration gel clearance formed by the spacer. Incidentally, each of the samples was injected after 1 ml of a solution formed by dissolving 7.5 mg of tris-aminomethane, 20 mg of SDS, 0.05 ml of β-mercaptoethanol and 2 mg of the sample into pure water had been heat-treated at 100° C. for 2 minutes. After injection of the samples, one drop of 0.5% Bromophenol Blue (containing 70% of glycerol and 5 mM of tris-aminomethane and having a pH value of 7.0) was added and sufficiently mixed, and an electrolyte was quietly superposed.

The top and bottom ends of the so obtained sample gel were immersed in an electrolyte consisting of an aqueous solution containing 0.025M of tris-aminomethane, 0.192M of glycine and 0.1% (W/V) of SDS, and the top end was connected to a cathode and the bottom end was connected to an anode and a constant current of 20 mA was applied for 20 hours while the plate gel was being cooled by city service water.

After stopping of application of the electric current, the plate gel was taken out from the electrophoresis tank, dyed with 0.25% Coomassie Brilliant Blue R-250 and decolorized by a mixed liquid of ethanol/acetic acid/water (25/8/65). The obtained results were analyzed to obtain FIG. 1.

Protein separation states of the molecular weight marker, rat serum and rat liver extract by SDS gel slab electrophoresis are illustrated in order from the left in FIG. 1. The SDS-treated proteins undergo the molecular sieve action of the polyacrylamide gel, and they are separated from the anode to the cathode in order of from lower molecular weights to higher molecular weights.

When the migration distance (cm) of the molecular weight marker from the top end of the plate gel is plotted on the ordinate and the logarithm of the molecular weight of the molecular weight marker, log (molecular weight$\times 10^{-4}$), is plotted on the abscissa, a standard curve as shown in FIG. 1 is obtained. From this standard curve, molecular weights of proteins can easily be determined based on the migration distances. For example, it can easily be known that the molecular weight of the component A in the rat serum is 26,195 and the molecular weight of the component B in the rat liver extract is 52,480, as is seen from FIG. 1. Similarly, molecular weights of other components can easily be determined from the migration distances thereof.

EXAMPLE 2

Molecular sieve chromatography was carried out in a column of Urotro Gel ACA 34 (trademark of the product supplied by LKB Co., Sweden) by using a reference product of hexikinase (derived from yeast) and a reference product (derived from yeast) of glucose-6-phosphate dehydrogenase as samples and a combination of a decamer (having a molecular weight of 24,110) of hempolypeptide obtained by decomposing equine heart muscle cytochrome C with chymotrypsin, a cytochrome C-albumin composite (having a molecular weight of 80,000) and a dimer (having a molecular weight of 160,000) of a cytochrome C-albumin composite as the molecular weight marker according to the following procedures.

In a 0.1M phosphate buffer solution (having a pH value of 7.5) was incorporated 500 ml of Urotro Gel, and the mixture was sufficiently degasified in a desiccator and quietly packed in a column (having a diameter of 25 mm and a length). Then, 1.5 l of a 0.1M phosphate buffer solution (having a pH value of 7.5) was caused to flow in the column to effect equilibration.

Then, 10 mg each of the above-mentioned three components of the molecular weight marker and 1 mg each of the above-mentioned two reference products of the enzymes were dissolved in 5 ml of a 0.1M phosphate buffer solution, and the solution was packed in the column.

Then, the elution treatment was carried out by supplying a 0.1M phosphate buffer solution as the developing solution at a flow rate of 15 ml/hr by using a metering pump. The eluate was fractionated by a fraction collector so that the volume of one fraction was 2.5 ml.

After completion of elution of all the proteins, the absorbance at 550 nm (the absorption wave length of cytochrome C) and the enzymatic activity (increase of the absorbance at 340 nm) were measured with respect to each fraction. Each of the molecular weight marker components had an absorption wave length of 550 nm, and these components underwent the molecular sieve action of the gel. Accordingly, the components were gradually dissolved out in order of the molecular weight.

Figure 2:
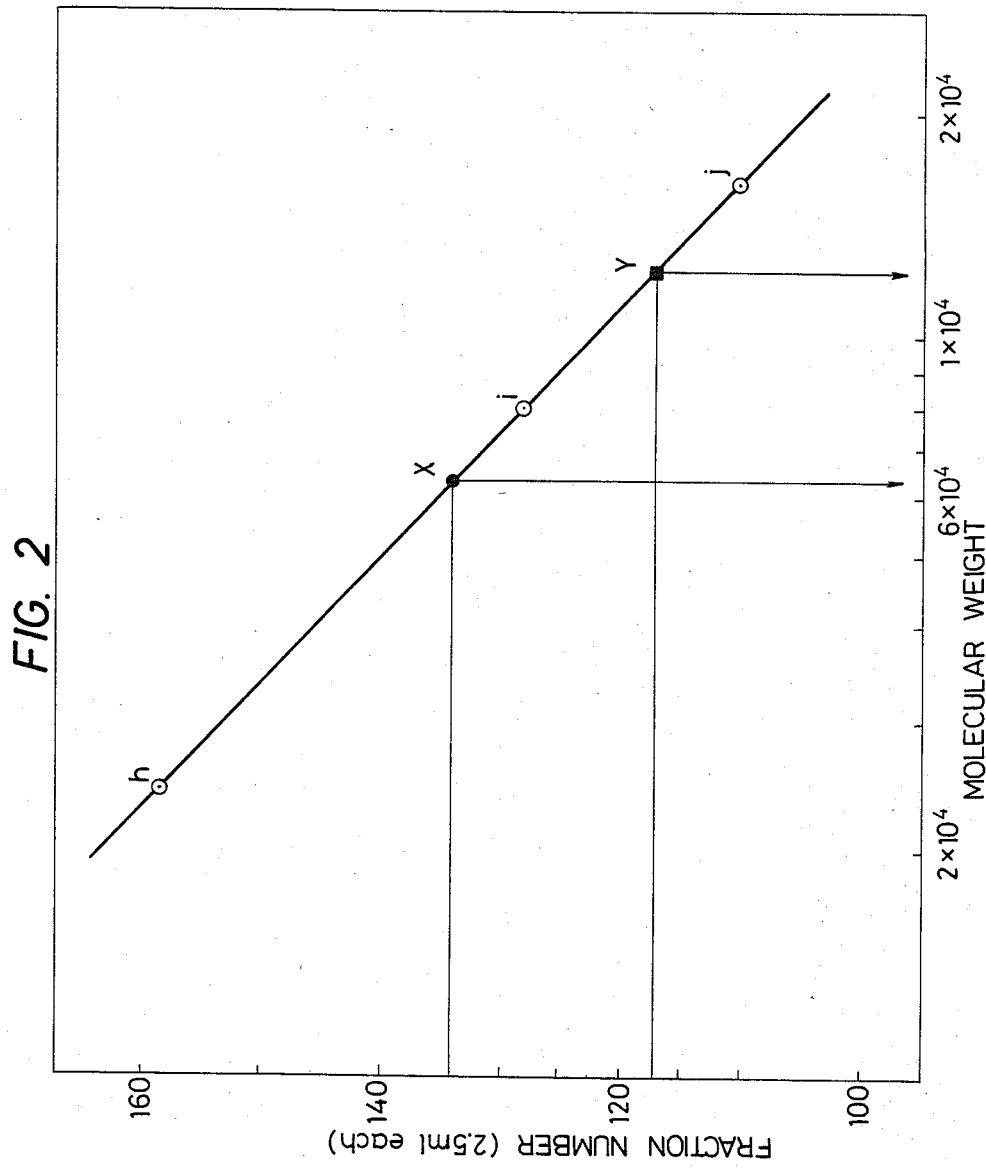
FIG. 2 is a diagram illustrating the results of Example 2 where the molecular weights of hexokinase and glucose-6-phosphate dehydrogenase were determined according to the molecular sieve chromatography method using the molecular weight marker of the present invention.

When the fraction numbers (the amounts of the liquids dissolved out) where the absorbances of these three molecular weight marker components were highest and molecular weights were plotted on a semilogarithmic chart, a standard line shown in FIG. 2 was obtained.

The hexokinase and glucose-6-phosphate dehydrogenase showed maximum activities in fractions No. 134 and No. 117, respectively. When these fraction numbers were plotted on the standard line shown in FIG. 2, it was found that the molecular weights of the hexokinase and glucose-6-phosphate dehydrogenase were 64,000 and 128,000, respectively.

As will be apparent from the foregoing description, it will readily be understood that if the colored protein molecular weight marker of the present invention is used, determination of the molecular weights can be accomplished very easily, and that the colored protein molecular weight marker of the present invention can be utilized effectively for determination of molecular weights by molecular sieve chromatography.

What is claimed is:

1. A colored molecular weight marker for molecular sieve chromatography, which comprises at least one member selected from the group consisting of:
   (1) a monomer of the equine heart muscle cytochrome C having a molecular weight of 12,300 or an oligomer or polymer consisting of at least two molecules of said equine heart muscle cytochrome C,
   (2) a monomer of a colored protein having a molecular weight of 1,800 which is obtained by treating the equine heart muscle cytochrome C with trypsin, or a colored protein having a molecular weight of 2,400 which is obtained by treating the equine heart muscle cytochrome C with chymotrypsin, or an oligomer or polymer consisting of at least two molecules of said colored protein having a molecular weight of 1,800 or of said colored protein having a molecular weight of 2,400,
   (3) a composite obtained by coupling said monomer, oligomer or polymer (1) with said monomer, oligomer or polymer (2),
   (4) a composite obtained by coupling said monomer, oligomer or polymer (1) and/or said monomer, oligomer or polymer (2) with bovine serum albumin having a molecular weight of 68,000,
   (5) an oligomer or polymer consisting of at least two molecules of said composite (3), and
   (6) an oligomer or polymer consisting of at least two molecules of said composite (4),
   with the proviso that said marker is not a monomer of equine heart muscle cytochrome C having a molecular weight of 12,300, alone,
   wherein the residual Schiff bases present in each said oligomer, polymer and composite have been converted into secondary amines, and wherein the amino residues of each said marker component are acetylated or succinylated to an extent sufficient to avoid being adsorbed on the carrier for the molecular sieve chromatography.

2. A colored molecular weight marker for molecular sieve chromatography, obtained by coupling equine heart muscle cytochrome C having a molecular weight of 12,300 or an oligomer or polymer thereof; a monomer of a colored protein having a molecular weight of 1,800, which is obtained by treating the equine heart muscle cytochrome C with trypsin, or an oligomer or polymer thereof; or a monomer of a colored protein having a molecular weight of 2,400 which is obtained by treating the equine heart muscle cytochrome C with chymotrypsin, or an oligomer or polymer thereof; with bovine serum albumin having a molecular weight of 68,000, wherein the residual Schiff bases present in said coupled marker have been converted into secondary amines, and wherein the amino residues of said coupled marker are acetylated or succinylated to an extent sufficient to avoid being adsorbed on the carrier for the molecular sieve chromatography.

3. A colored molecular weight marker combination for molecular sieve chromatography, which comprises at least two members selected from the group consisting of:
   (1) a monomer of equine heart muscle cytochrome C having a molecular weight of 12,300 or an oligomer or polymer consisting of at least two molecules of said equine heart muscle cytochrome C,
   (2) a monomer of a colored protein having a molecular weight of 1,800 which is obtained by treating the equine heart muscle cytochrome C with trypsin, or a colored protein having a molecular weight of 2,400 which is obtained by treating the equine heart muscle cytochrome C with chymotrypsin, or an oligomer or polymer consisting of at least two molecules of said colored protein having a molecular weight of 1,800 or of said colored protein having a molecular weight of 2,400,
   (3) a composite obtained by coupling said monomer, oligomer or polymer (1) with said monomer, oligomer or polymer (2),
   (4) a composite obtained by coupling said monomer, oligomer or polymer (1) and/or said monomer, oligomer or polymer (2) with bovine serum albumin having a molecular weight of 68,000,
   (5) an oligomer or polymer consisting of at least two molecules of said composite (3), and
   (6) an oligomer or polymer consisting of at least two molecules of said composite (4),
   wherein the residual Schiff bases present in each said oligomer, polymer and composite have been converted into secondary amines, and wherein the amino residues of each said marker component are acetylated or succinylated to an extent sufficient to avoid being adsorbed on the carrier for the molecular sieve chromatography.

4. A colored molecular weight marker combination for molecular sieve chromatography, as set forth in claim 3, including at least three of said members, each having a different molecular weight and covering a broad range of molecular weights.

5. A colored molecular weight marker combination for molecular sieve chromatography, as set forth in claim 3, including at least seven of said members, each having a different molecular weight and covering a broad range of molecular weights.

6. A method for purifying a protein sample of known molecular weight using the colored molecular weight marker combination for molecular sieve chromatography in accordance with claim 3, comprising:
   selecting the members of the group comprising said colored molecular weight marker combination such that said combination contains only two members, one member having a molecular weight above that of said protein sample and a second member having a molecular weight below that of said protein sample;
   subjecting the protein sample and said colored molecular weight marker combination to molecular sieve chromatgraphy; and
   recovering the protein eluted between the elution of the members of said colored molecular weight marker combination.

7. A colored molecular weight marker for SDS electrophoresis, which comprises at least one member selected from the group consisting of:
   (1) a monomer of the equine heart muscle cytochrome C having a molecular weight of 12,300 or an oligomer or polymer consisting of at least two molecules of said equine heart muscle cytochrome C,
   (2) a monomer of a colored protein having a molecular weight of 1,800 which is obtained by treating the equine heart muscle cytochrome C with trypsin, or a colored protein having a molecular weight of 2,400 which is obtained by treating the equine heart muscle cytochrome C with chymotrypsin, or an oligomer or polymer consisting of at least two molecules of said colored protein having a molecular weight of 1,800 or of said colored protein having a molecular weight of 2,400,
   (3) a composite obtained by coupling said monomer, oligomer or polymer (1) with said monomer, oligomer or polymer (2),
   (4) a composite obtained by coupling said monomer, oligomer or polymer (1) and/or said monomer, oligomer or polymer (2) with bovine serum albumin having a molecular weight of 68,000,
   (5) an oligomer or polymer consisting of at least two molecules of said composite (3), and
   (6) an oligomer or polymer consisting of at least two molecules of said composite (4),
   with the proviso that said marker is not a monomer of equine heart muscle cytochrome C having a molecular weight of 12,300, alone,
   wherein the residual Schiff bases present in each said oligomer, polymer and composite have been converted into secondary amines.

8. A colored molecular weight marker for SDS electrophoresis, obtained by coupling
   (a) equine heart muscle cytochrome C having a molecular weight of 12,300 or an oligomer or polymer thereof,
   (b) a monomer of a colored protein having a molecular weight of 1,800, which is obtained by treating the equine heart muscle cytochrome C with trypsin, or an oligomer or polymer thereof, or
   (c) a monomer of a colored protein having a molecular weight of 2,400 which is obtained by treating the equine heart muscle cytochrome C with chymotrypsin, or an oligomer or polymer thereof, with bovine serum albumin having a molecular weight of 68,000,
   wherein the residual Schiff bases present in said coupled marker have been converted into secondary amines.

9. A colored molecular weight marker combination for SDS electrophoresis, which comprises at least two members selected from the group consisting of:
   (1) a monomer of equine heart muscle cytochrome C having a molecular weight of 12,300 or an oligomer or polymer consisting of at least two molecules of said equine heart muscle cytochrome C,
   (2) a monomer of a colored protein having a molecular weight of 1,800 which is obtained by treating the equine heart muscle cytochrome C with trypsin, or a colored protein having a molecular weight of 2,400 which is obtained by treating the equine heart muscle cytochrome C with chymotrypsin, or an oligomer or polymer consisting of at least two molecules of said colored protein having a molecular weight of 1,800 or of said colored protein having a molecular weight of 2,400,
   (3) a composite obtained by coupling said monomer, oligomer or polymer (1) with said monomer, oligomer or polymer (2),
   (4) a composite obtained by coupling said monomer, oligomer or polymer (1) and/or said monomer, oligomer or polymer (2) with bovine serum albumin having a molecular weight of 68,000,
   (5) an oligomer or polymer consisting of at least two molecules of said composite (3), and
   (6) an oligomer or polymer consisting of at least two molecules of said composite (4),
   wherein the residual Schiff bases present in each said oligomer, polymer and composite have been converted into secondary amines.

10. A colored molecular weight marker combination for SDS electrophoresis, as set forth in claim 9, including at least three of said members, each having a different molecular weight and covering a broad range of molecular weights.

11. A colored molecular weight marker combination for SDS electrophoresis, as set forth in claim 9, including at least seven of said members, each having a different molecular weight and covering a broad range of molecular weights.

12. A method for purifying a protein sample of known molecular weight using the colored molecular weight marker combination for SDS electrophoresis in accordance with claim 9, comprising:
   selecting the members of the group comprising said colored molecular weight marker combination such that said combination contains only two members, one member having a molecular weight above that of said protein sample and second member having a molecular weight below that of said protein sample;
   subjecting the protein sample and said colored molecular weight marker combination to SDS electrophoresis; and
   recovering the protein positioned between the positions of the members of said colored molecular weight marker combination.

* * * * *